United States Patent
Mun et al.

(10) Patent No.: US 10,392,449 B2
(45) Date of Patent: Aug. 27, 2019

(54) POLYMERIZATION INITIATOR, MODIFIED CONJUGATED DIENE-BASED POLYMER, AND METHODS FOR PREPARING THEM

(71) Applicant: LG Chem, Ltd., Seoul (KR)

(72) Inventors: Min Sik Mun, Daejeon (KR); No Ma Kim, Daejeon (KR); Ho Young Lee, Daejeon (KR)

(73) Assignee: LG Chem, Ltd. (KR)

( * ) Notice: Subject to any disclaimer, the term of this patent is extended or adjusted under 35 U.S.C. 154(b) by 180 days.

(21) Appl. No.: 15/566,285

(22) PCT Filed: Nov. 2, 2016

(86) PCT No.: PCT/KR2016/012519
§ 371 (c)(1),
(2) Date: Oct. 13, 2017

(87) PCT Pub. No.: WO2017/115996
PCT Pub. Date: Jul. 6, 2017

(65) Prior Publication Data
US 2018/0112015 A1   Apr. 26, 2018

(30) Foreign Application Priority Data

Dec. 28, 2015  (KR) .................. 10-2015-0187677
Oct. 31, 2016  (KR) .................. 10-2016-0143543

(51) Int. Cl.

| | | |
|---|---|---|
| C08C 19/44 | (2006.01) | |
| B60C 1/00 | (2006.01) | |
| C07F 1/02 | (2006.01) | |
| C08F 36/06 | (2006.01) | |
| C08C 19/25 | (2006.01) | |
| C08F 212/08 | (2006.01) | |
| C08K 3/04 | (2006.01) | |
| C08K 3/36 | (2006.01) | |
| C08L 9/00 | (2006.01) | |
| C08L 9/06 | (2006.01) | |
| C08C 19/26 | (2006.01) | |
| C08F 4/48 | (2006.01) | |
| C08F 136/06 | (2006.01) | |
| C07F 1/04 | (2006.01) | |
| C07F 1/06 | (2006.01) | |

(52) U.S. Cl.
CPC ............ *C08C 19/44* (2013.01); *B60C 1/00* (2013.01); *C07F 1/02* (2013.01); *C08C 19/25* (2013.01); *C08C 19/26* (2013.01); *C08F 4/48* (2013.01); *C08F 4/488* (2013.01); *C08F 36/06* (2013.01); *C08F 136/06* (2013.01); *C08F 212/08* (2013.01); *C08K 3/04* (2013.01); *C08K 3/36* (2013.01); *C08L 9/00* (2013.01); *C08L 9/06* (2013.01)

(58) Field of Classification Search
USPC .................. 260/665 R; 564/461; 526/180
See application file for complete search history.

(56) References Cited

U.S. PATENT DOCUMENTS

| | | | |
|---|---|---|---|
| 3,317,918 A | | 5/1967 | Foster et al. |
| 3,326,881 A | * | 6/1967 | Uraneck .................. C08F 4/06 526/173 |
| 4,067,917 A | | 1/1978 | Sigwalt et al. |
| 5,171,800 A | * | 12/1992 | Bronstert ................. C07F 1/00 525/250 |
| 5,464,914 A | | 11/1995 | Lo et al. |
| 8,207,282 B2 | * | 6/2012 | Yoon ..................... C07F 7/1804 526/173 |
| 2003/0181747 A1 | | 9/2003 | Li et al. |
| 2009/0326176 A1 | | 12/2009 | Yon |

FOREIGN PATENT DOCUMENTS

| | | |
|---|---|---|
| JP | S5331859 U | 3/1978 |
| JP | H06271706 A | 9/1994 |
| JP | 2004002249 A | 1/2004 |
| WO | 2015010710 A1 | 1/2015 |

OTHER PUBLICATIONS

Extended European Search Report including Written Opinion for Application No. EP16881949.8 dated May 2, 2018.
Search report from International Application No. PCT/KR2016/012519, dated Feb. 2, 2017.
Elkins, C. L., et al., "Living Anionic Polymerization of Hexamethylcyclotrisiloxane (D3) Using Functionalized Initiation," Macromolecules, [Electronic Publishing] Jul. 29, 2004, vol. 37, No. 17, pp. 6657-6659.

* cited by examiner

*Primary Examiner* — Fred M Teskin
(74) *Attorney, Agent, or Firm* — Lerner, David, Littenberg, Krumholz & Mentlik, LLP

(57) ABSTRACT

The present invention relates to a polymerization initiator represented by Formula 1, a modified conjugated diene-based polymer, methods for preparing them, a rubber composition comprising the modified conjugated diene-based polymer, and a tire prepared from the rubber composition.

[Formula 1]

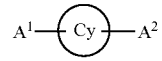

(In Formula 1, the definition of each substituent is the same as defined in the description.)

18 Claims, No Drawings

POLYMERIZATION INITIATOR, MODIFIED CONJUGATED DIENE-BASED POLYMER, AND METHODS FOR PREPARING THEM

CROSS-REFERENCE TO RELATED APPLICATIONS

The present application is a national phase entry under 35 U.S.C. § 371 of International Application No. PCT/KR2016/012519, filed Nov. 2, 2016, which claims priority from Korean Patent Application No. 10-2015-0187677, filed on 28 Dec. 2015, and Korean Patent Application No. 10-2016-0143543, filed on 31 Oct. 2016, the entire contents of which are incorporated herein by reference.

TECHNICAL FIELD

The present invention relates to a polymerization initiator, a modified conjugated diene-based polymer, methods for preparing them, a rubber composition comprising the modified conjugated diene-based polymer, and a tire prepared from the rubber composition.

BACKGROUND ART

Recently, conjugated diene-based polymers having low running resistance, and excellent abrasion resistance and wet traction are required as rubber materials for tires. In order to decrease the running resistance of tires, the hysteresis loss of a vulcanized rubber is required to decrease. As such rubber materials having low hysteresis loss, natural rubbers are known, but these materials have defects of low wet traction. Recently, a conjugated diene-based polymer such as a styrene-butadiene rubber (hereinafter, will be referred to as SBR) and a butadiene rubber (hereinafter, will be referred to as BR) prepared by an emulsion polymerization or a solution polymerization is used as rubbers for tires.

Meanwhile, a solution polymerization SBR is prepared using an anion polymerization initiator, and in this case, an alkyl lithium is mainly used as the anion polymerization initiator.

However, with regard to the above-described rubbers for tires, the improvement of hysteresis loss or abrasion resistance is insufficient, improving effects by mixing are small, and processability is rather decreased.

Accordingly, development of a polymerization initiator having sufficient improvement of abrasion resistance and excellent processability, and a rubber having excellent exothermic properties together with excellent physical properties such as tensile strength, abrasion resistance and wet traction when mixed silica by using the same, is required.

DISCLOSURE OF THE INVENTION

Technical Problem

The present invention has been devised to solve the above-mentioned problems of the conventional technique, and an object of the present invention is to provide a modified polyfunctional polymerization initiator.

Another object of the present invention is to provide a method for preparing the polymerization initiator.

Further another object of the present invention is to provide a modified conjugated diene-based polymer using the polymerization initiator.

Further another object of the present invention is to provide a modified conjugated diene-based polymer prepared by the method, having excellent exothermic properties, and at the same time, being capable of improving tensile strength, abrasion resistance, and wet traction.

Technical Solution

To solve the above-described tasks, the present invention provides a polymerization initiator comprising a compound represented by the following Formula 1:

[Formula 1]

[Formula 2]

in Formula 1, Cy may be a cyclic saturated hydrocarbon group having from 5 to 8 carbon atoms, which is unsubstituted or substituted with an alkyl group having from 1 to 4 carbon atoms, and $A^1$ and $A^2$ may be each independently a functional group represented by Formula 2, in Formula 2, R may be a linear hydrocarbon group having from 1 to 20 carbon atoms, or a cyclic saturated hydrocarbon group having from 3 to 20 carbon atoms, X may be a divalent hydrocarbon group having from 1 to 5 carbon atoms, M may be an alkali metal, and a may be 0 or 1.

In addition, the present invention provides a method for preparing a polymerization initiator comprising reacting a compound represented by the following Formula 1a and a compound represented by Formula 4 in a solvent to prepare a compound represented by Formula 1b by (S1); and reacting the compound represented by Formula 1b and an alkali metal or a compound represented by the following Formula 5 (S2):

[Formula 1a]

[Formula 1b]

in Formulae 1a and 1b,

Cy may be a cyclic saturated hydrocarbon group having from 5 to 8 carbon atoms, which is unsubstituted or substituted with an alkyl group having from 1 to 4 carbon atoms, $A^{1\prime}$ and $A^{2\prime}$ may be each independently a functional group represented by Formula 2a, and $A^{1\prime\prime}$ and $A^{2\prime\prime}$ may be each independently a functional group represented by Formula 2b,

[Formula 2a]

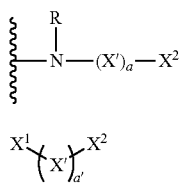
[Formula 2b]

[Formula 4]

in Formulae 2a, 2b and 4,

R may be a linear hydrocarbon group having from 1 to 20 carbon atoms, or a monocyclic or multicyclic saturated hydrocarbon group having from 3 to 20 carbon atoms, X' may be a divalent hydrocarbon group having from 1 to 5 carbon atoms, a' may be 0 or 1, and $X^1$ and $X^2$ may be each independently a halogen compound, $R'(M)_x$ [Formula 5]

in Formula 5,

R' may be a hydrocarbyl group having from 1 to 20 carbon atoms, M may be an alkali metal, and x may be an integer selected from 1 to 4.

In addition, the present invention provides a modified conjugated diene-based polymer comprising a functional group derived from the polymerization initiator represented by Formula 1 at one terminal, and a method for preparing the same.

Further, the present invention provides a rubber composition comprising the modified conjugated diene-based polymer, and a tire manufactured using the rubber composition.

Advantageous Effects

A conjugated diene-based polymer with high vinyl content and excellent physical properties may be obtained by applying a modified polyfunctional polymerization initiator represented by Formula 1 according to the present invention.

The polymerization initiator has a plurality of functional groups and is capable of forming a polymer having a plurality of active parts and improving reactivity with a modifier. Accordingly, a modified conjugated diene-based polymer may be prepared in a high modification ratio. As a result, affinity with a filler which is added to a tire rubber composition may be improved as well as physical properties such as tensile strength, abrasion resistance and wet traction.

BEST MODE FOR CARRYING OUT THE INVENTION

Hereinafter, the present invention will be explained in particular referring to embodiments and experimental embodiments. However, the following embodiments and experimental embodiments are only for the illustration of the present invention, and the scope of the present invention is not limited thereto.

Preparation Example: Preparation of Polymerization Initiator of Formula 3-1 Below To a 3 L, four-neck round-bottomed flask to which an agitator, a thermometer, a dropping funnel and a Schlenk line were connected, 8 mol (1105.68 g) of potassium carbonate was added, the pressure was reduced, and moisture was completely removed. Then, under an argon atmosphere, 4 mol (629.76 g) of 1-bromo-3-chloropropane, 1 mol (88.15 g) of t-butyl methyl ether, and 1 mol (84.16 g) of cyclohexane were added thereto and stirred at 0° C. at 300 rpm. 2.4 mol (341.38 g) of N,N'-dimethyl-1,2-cyclohexanediamine was injected thereto via a dropping funnel over 1 hour, and after completing the injection, the temperature was elevated to room temperature and the reaction was performed. After completing the reaction, 400 ml of cyclohexane was added and sufficiently stirred, and then, remaining HBr was removed using a sodium hydrogen carbonate saturated aqueous solution. After that, salts were removed using distilled water and brine, and remaining water was removed using sodium sulfate. Sodium sulfate was removed using a filter, and solvents were removed using a rotary evaporator. Then, a separated intermediate was obtained via distillation.

Under an argon atmosphere, a lithium metal cut into small pieces was injected into a three-neck round-bottomed flask, and a thermometer, a dropping funnel, and a Schlenk line were respectively connected. After injecting a solvent, the flask was heated to a predetermined temperature, and the intermediate diluted in a solvent was slowly added. After completing the reaction, lithium chloride was removed via filtering, and solvents were removed under a reduced pressure to prepare a polymerization initiator represented by Formula 3-1.

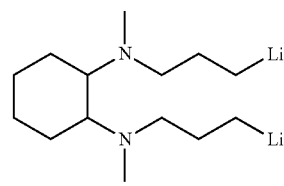
[Formula 3-1]

Example 1: Preparation of Modified Conjugated Diene-Based Polymer

To a 20 L autoclave reactor, 270 g of styrene, 710 g of 1,3-butadiene, 5000 g of n-hexane, and 0.9 g of 2,2-bis(2-oxolanyl)propane as a polar additive were added, and the inner temperature of the reactor was elevated to 40° C. When the inner temperature of the reactor reached 40° C., 4.3 mmol of a compound represented by Formula 1-1, which was prepared in Example 1 was injected into the reactor, and an adiabatic heating was performed. After finishing the adiabatic heating and after about 20 minutes, 20 g of 1,3-butadiene was injected. After 5 minutes, 4.3 mmol of bis(diethoxymethylsilylpropyl)-N-methylamine was injected and reacted for 15 minutes. Then, the polymerization reaction was quenched using ethanol, and 45 ml of a hexane solution in which 0.3 wt % of a butylated hydroxytoluene (BHT) antioxidant was dissolved was added thereto. The polymer thus obtained was injected into hot water heated with steam, stirred to remove solvents, and roll dried to remove remaining solvents and water to prepare a modified conjugated diene-based polymer. Analysis results on the modified conjugated diene-based polymer thus prepared are shown in Table 1 below.

Example 2: Preparation of Modified Conjugated Diene-Based Polymer

A modified conjugated diene-based polymer was prepared by performing the same method described in Example 1 except for using N,N-bis(triethoxysilylpropyl)aminopropyl-1-imidazole instead of bis(diethoxymethylsilylpropyl)-N-methylamine.

Comparative Example 1: Preparation of Modified Conjugated Diene-Based Polymer A modified conjugated diene-based polymer was prepared by performing the same method described in Example 1 except for using n-butyllithium instead of the compound represented by Formula 3-1.

Comparative Example 2: Preparation of Modified Conjugated Diene-Based Polymer A modified conjugated diene-based polymer was prepared by performing the same method described in Comparative Example 1 except for using N,N-bis(triethoxysilylpropyl) aminopropyl-1-imidazole instead of bis(diethoxymethylsilylpropyl)-N-methylamine.

Comparative Example 3: Preparation of Modified Conjugated Diene-Based Polymer A modified conjugated diene-based polymer was prepared by performing the same method described in Comparative Example 1 except for using a compound represented by Formula 26 below instead of the compound represented by Formula 3-1.

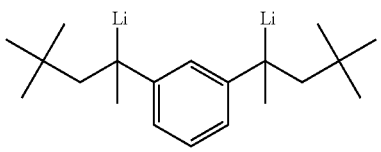

[Formula 26]

Experimental Example 1

Weight average molecular weight (Mw), number average molecular weight (Mn), molecular weight distribution (MWD), and mooney viscosity (MV) were measured for each of the modified conjugated diene-based polymers prepared in the examples and the comparative examples. The results are shown in Table 1 below.

The weight average molecular weight (Mw), and the number average molecular weight (Mn) were measured by gel permeation chromatography (GPC) analysis, and the molecular weight distribution (MWD, Mw/Mn) was obtained by calculating from each of the measured molecular weights. Particularly, the GPC used two columns of PLgel Olexis (Polymer Laboratories Co. Ltd.) and one column of PLgel mixed-C (Polymer Laboratories Co. Ltd.) in combination, and newly replaced columns were all mixed bed type columns. In addition, polystyrene (PS) was used as a GPC standard material for calculating the molecular weight.

The mooney viscosity (MV, (ML1+4 @100° C.) MU) was measured by using MV-2000 (Alpha Technologies Co., Ltd.) using Large Rotor at a rotor speed of 2±0.02 rpm and 100° C. In this case, a specimen used was stood at room temperature (23±3° C.) for 30 minutes or more, and 27±3 g of the specimen was collected and put in a die cavity, and then, Platen was operated, and the mooney viscosity was measured for 4 minutes.

TABLE 1

| | | Division | | | | |
|---|---|---|---|---|---|---|
| | | Example | | Comparative Example | | |
| | | 1 | 2 | 1 | 2 | 3 |
| Molecular weight ($\times 10^3$) | Number average molecular weight (g/mol) | 305 | 386 | 301 | 384 | 307 |
| | Weight average molecular weight (g/mol) | 397 | 555 | 390 | 553 | 397 |
| | Molecular weight distribution | 1.3 | 1.4 | 1.3 | 1.4 | 1.3 |
| | Mooney viscosity | 68 | 89 | 68 | 88 | 88 |

Experimental Example 2

In order to comparatively analyze the physical properties of a rubber composition comprising each of the modified conjugated diene-based copolymers prepared in the examples and the comparative examples and a molded product manufactured therefrom, tensile properties, abrasion resistance and wet traction were measured, respectively. The results are listed in Table 2 below.

1) Preparation of Rubber Composition

Each rubber composition was prepared via a first stage mulling and a second stage mulling. In this case, the amounts used of materials excluding the modified conjugated diene-based copolymer were shown based on 100 parts by weight of the modified conjugated diene-based copolymer. In the first stage mulling, 137.5 parts by weight of each modified conjugated diene-based copolymer, 70 parts by weight of silica, 11.2 parts by weight of bis(3-triethoxysilylpropyl)tetrasulfide as a silane coupling agent, 25 parts by weight of a process oil (TDAE), 2 parts by weight of an antiaging agent (TMDQ), 3 parts by weight of zinc oxide (ZnO), 2 parts by weight of stearic acid, and 1 part by weight of wax were mixed using a banbury mixer equipped with a temperature controlling apparatus. In this case, the temperature of the mulling apparatus was controlled, and a first mixture was obtained at a discharge temperature of 150° C. In the second stage mulling, the first mixture was cooled up to room temperature, and 1.75 parts by weight of a rubber accelerator (CZ), 1.5 parts by weight of a sulfur powder, and 2 parts by weight of a vulcanization accelerator were added to the mulling apparatus, a curing process was performed at 150° C. for 20 minutes to prepare a rubber composition. In this case, the silica used has a nitrogen adsorption specific surface area of 175 m$^2$/g, and CTAB adsorption value of 160 m$^2$/g.

2) Tensile Properties

Tensile properties were measured by manufacturing each specimen and measuring tensile strength when broken and tensile stress when elongated by 300% (300% modulus) of each specimen according to an ASTM 412 tensile test method. Particularly, the tensile properties were measured using a Universal Test machine 4204 (Instron Co., Ltd.) tensile tester at room temperature and a rate of 50 cm/min.

3) Abrasion Resistance

Abrasion amount was measured for a load of 6 pounds and 1000 rotations using an Akron abrasion tester and indexed. The smaller the index value, the better the abrasion resistance 4) Viscoelasticity Properties Viscoelasticity properties were obtained by measuring Tan δ by changing deformation at each measurement temperature (−60° C. to 60° C.) with a twist mode and a frequency of 10 Hz using a dynamic mechanical analyzer (TA Co., Ltd.). Payne effect was shown as a difference between a minimum value and a maximum value at deformation of 0.28% to 40%. If the Tan δ at a low temperature of 0° C. is high, it means that wet traction is good, and if the Tan δ at a high temperature of 60° C. is low, it means that hysteresis loss is small and low rolling resistance (fuel consumption ratio) is good.

5) Vulcanization Properties

Vulcanization properties (t90) were obtained by measuring the time required (t90) until reaching an MH (maximum torque) value and 90% vulcanization during vulcanizing at 150° C. for 50 minutes by using a moving die rheometer (MDF).

TABLE 2

| | | Division | | | |
|---|---|---|---|---|---|
| | | Example | | Comparative Example | | |
| | | 1 | 2 | 1 | 2 | 3 |
| Vulcanization properties (t90 min) | | 21.1 | 21.4 | 21.7 | 21.9 | 21.1 |
| Visco-elasticity | tanδ @0° C. | 1.12+ | 1.126 | 0.998 | 1.003 | 1.021 |
| | tanδ @60° C. | 0.094 | 0.099 | 0.108 | 0.109 | 0.104 |
| Tensile properties | 300% modulus (kgf/cm²) | 161 | 170 | 151 | 156 | 151 |
| | Tensile strength (kgf/cm²) | 189 | 187 | 177 | 174 | 179 |
| Abrasion resistance | | 92 | 89 | 100 | 98 | 99 |

As shown in Table 2, it was secured that the vulcanization time of rubber compositions comprising the modified conjugated diene-based polymers of Example 1 and Example 2, which were prepared using an initiator comprising an amine according to an embodiment of the present invention, is shorter by about 0.5 minutes than that of Comparative Example 1 and Comparative Example 2.

In addition, the tensile properties and viscoelasticity of the rubber compositions comprising the modified conjugated diene-based polymers of Example 1 and Example 2, which were prepared using the modifier according to an embodiment of the present invention were secured to be better than those of the rubber compositions comprising the conjugated diene-based polymers of Comparative Examples 1 to 3.

Particularly, it was secured that the rubber compositions comprising the modified conjugated diene-based polymers of Example 1 and Example 2, which were prepared using the modifier according to an embodiment of the present invention had an increased Tan δ value at 0° C. (increased by about 13% degree) and a decreased Tan δ value at 60° C. (decreased by about 13% and 10% degrees) when compared to the rubber compositions comprising the conjugated diene-based polymers of Comparative Example 1 and Comparative Example 2. In addition, the Tan δ value at 0° C. was increased (increased by about 6% degree) and the Tan δ value at 60° C. was decreased (decreased by about 10% degree) when compared to the rubber composition comprising the conjugated diene-based polymer of Comparative Example 3. The results mean that the modified conjugated diene-based polymer according to an embodiment of the present invention shows excellent surface resistance and running resistance, and high consumption ratio.

BEST MODE FOR CARRYING OUT THE INVENTION

Hereinafter, the present invention will be explained in more detail to assist the understanding of the present invention.

It will be understood that words or terms used in the specification and claims shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

The present invention provides a polymerization initiator comprising a compound represented by Formula 1 below.

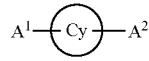

[Formula 1]

In Formula 1, Cy may be a cyclic saturated hydrocarbon group having from 5 to 8 carbon atoms, which is unsubstituted or substituted with an alkyl group having from 1 to 4 carbon atoms, and $A^1$ and $A^2$ may be each independently represented by a functional group represented by Formula 2 below.

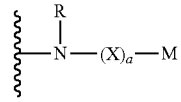

[Formula 2]

In Formula 2, R may be a linear hydrocarbon group having from 1 to 20 carbon atoms, or a monocyclic or multicyclic saturated hydrocarbon group having from 3 to 20 carbon atoms, X may be a divalent hydrocarbon group having from 1 to 5 carbon atoms, M may be an alkali metal, and a may be 0 or 1.

In a particular embodiment, in Formula 1, Cy may be an unsubstituted cyclic saturated hydrocarbon group having from 5 to 8 carbon atoms, and $A^1$ and $A^2$ may be each independently a functional group represented by Formula 2. In Formula 2, R may be a linear hydrocarbon group having from 1 to 6 carbon atoms, or a monocyclic or multicyclic saturated hydrocarbon group having from 4 to 8 carbon atoms, X may be a divalent hydrocarbon group having from 1 to 5 carbon atoms, M may be an alkali metal, and a may be 0 or 1.

The compound represented by Formula 1 may be, for example, a compound represented by Formula 3 below.

[Formula 3]

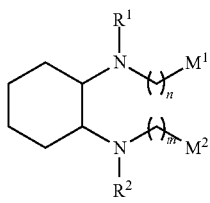

In Formula 3, $R^1$ and $R^2$ may be each independently a linear hydrocarbon group having from 1 to 20 carbon atoms, or a monocyclic or multicyclic saturated hydrocarbon group having from 4 to 20 carbon atoms, $M^1$ and $M^2$ may be each independently an alkali metal, and m and n may be each independently an integer selected from 0 to 5.

In a particular embodiment, $R^1$ and $R^2$ may be each independently a linear hydrocarbon group having from 1 to 6 carbon atoms, or may be combined with each other to form a monocyclic or multicyclic saturated hydrocarbon group having from 4 to 8 carbon atoms, and $M^1$ and $M^2$ may be each independently selected from Li, Na, K, Rb, and Cs.

In a more particular embodiment, in Formula 3, $R^1$ and $R^2$ may be each independently an alkyl group having from 1 to carbon atoms, and $M^1$ and $M^2$ may be each independently selected from Li, Na, and K.

According to an embodiment of the present invention, the compound represented by Formula 3 may be any one selected from the group consisting of the compounds represented by Formulae 3-1 to 3-4 below.

[Formula 3-1]

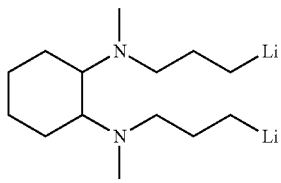

[Formula 3-2]

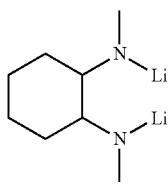

[Formula 3-3]

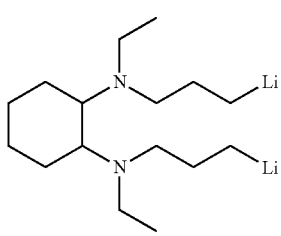

[Formula 3-4]

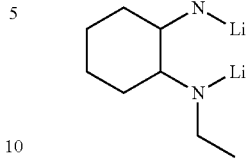

The polymerization initiator may be used for initiating the polymerization of various polymers. Particularly, in case of using the polymerization initiator for a conjugated diene-based polymer, high activity and sufficient randomization of monomers may be secured.

In addition, the present invention provides a method for preparing a polymerization initiator for preparing a polymerization initiator comprising the compound represented by Formula 1.

The method for preparing the polymerization initiator of the present invention comprises reacting a compound represented by Formula 1a below and a compound represented by Formula 4 in a solvent to prepare a compound represented by Formula 1b below by (S1); and reacting the compound represented by Formula 1b and an alkali metal or a compound represented by Formula 5 below (S2).

[Formula 1a]

[Formula 1b]

In Formulae 1a and 1b, Cy may be a cyclic saturated hydrocarbon group having from 5 to 8 carbon atoms, which is unsubstituted or substituted with an alkyl group having from 1 to 4 carbon atoms, $A'^1$ and $A'^2$ may be each independently a functional group represented by Formula 2a below, and $A''^1$ and $A''^2$ may be each independently a functional group represented by Formula 2b below.

[Formula 2a]

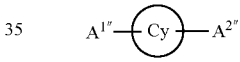

[Formula 2b]

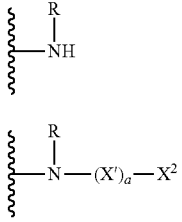

[Formula 4]

In Formulae 2a, 2b and 4, R may be a linear hydrocarbon group having from 1 to 20 carbon atoms, or a monocyclic or multicyclic saturated hydrocarbon group having from 3 to 20 carbon atoms, X' may be a divalent hydrocarbon group having from 1 to 5 carbon atoms, a' may be 0 or 1, and $X^1$ and $X^2$ may be each independently a halogen compound.

$R'(M)_x$ [Formula 5]

In Formula 5, R' may be a hydrocarbyl group having from 1 to 20 carbon atoms, M may be an alkali metal, and x may be an integer selected from 1 to 4.

In a particular embodiment, in Formulae 1a and 1b, Cy may be an unsubstituted cyclic saturated hydrocarbon group having from 5 to 8 carbon atoms, $A'^1$ and $A'^2$ may be each independently a functional group represented by Formula 2a, and $A'''^1$ and $A''^2$ may be each independently a functional group represented by Formula 2b. In Formulae 2a, 2b and 4, R may be a linear hydrocarbon group having from 1 to 6 carbon atoms, or a monocyclic or multicyclic saturated hydrocarbon group having from 4 to 8 carbon atoms, X' may be a divalent hydrocarbon group having from 1 to 5 carbon atoms, and a' may be 0 or 1, $X^1$ and $X^2$ may be each independently a halogen atom selected from the group consisting of F, Br, Cl and I. In Formula 5, R' may be a hydrocarbyl group having from 1 to 20 carbon atoms, M may be selected from Li, Na, K, Rb and Cs, and x may be an integer selected from 1 to 4.

In the method for preparing the polymerization initiator according to an embodiment of the present invention, the reaction in step (S1) may be performed in a reaction temperature of, for example, 0 to 50° C., 0 to 40° C., or 0 to 35° C., and within this range, effects of minimizing side reactions may be attained.

In step (S1), the reaction time may be from 12 minutes to 48 minutes, and within this range, effects of minimizing side reactions may be attained.

In step (S1), the molar ratio of the compound represented by Formula 1a and the compound represented by Formula 4 may be from 1:1 to 1:4, from 1:1 to 1:3, or from 1:1 to 1:1.8, and within this range, effects of minimizing side reactions may be attained.

In addition, the solvent may be a nonpolar solvent, and a polar solvent may be additionally added to increase solubility. In this case, the solubility of a solute may be increased and effects of promoting the reaction may be attained.

The polar solvent may comprise, for example, an ether-based solvents selected from the group consisting of tetrahydrofuran, ditetrahydrofurylpropane, diethyl ether, tert-butyl methyl ether, cyclo amalether, dipropyl ether, ethylene dimethyl ether, ethylene dimethyl ether, diethylene glycol, dimethyl ether, tert-butoxy ethoxy ethane, bis(2-dimethylaminoethyl)ether and (dimethylaminoethyl) ethyl ether, and more preferably, diethyl ether or tert-butyl methyl ether may be used.

The polar solvent may comprise, for example, saturated hydrocarbon-based solvents selected from the group consisting of hexane, heptane, octane, nonane, decane, cyclopentane, cyclohexane and cycloheptane, and more preferably, hexane or cyclohexane may be used.

The reaction in step (S2) may be performed in a reaction temperature of, for example, 0 to 70° C., and within this range, effects of minimizing side reactions may be attained.

In addition, in step (S2), the reaction time may be from 0.5 hours to 6 hours, and within this range, effects of minimizing side reactions may be attained.

Meanwhile, during the reaction of the compound represented by Formula 1b and the alkali metal in step (S2), the molar ratio of the compound represented by Formula 1b and the alkali metal may be from 1:10 to 1:40, and during the reaction of the compound represented by Formula 1b and the compound represented by Formula 5 in step (S2), the molar ratio of the compound represented by Formula 1b and the compound represented by Formula 5 may be from 1:1.9 to 1:2.2.

Within this range, side reactions may be minimized, and effects of obtaining the compound represented by Formula 1 in a high conversion ratio may be attained.

Meanwhile, during the reaction of step b, defects of increasing side reactions may occur if a polar solvent is present, and the reaction may be conducted in the absence of a polar solvent.

In addition, the present invention provides a method for preparing a modified conjugated diene-based polymer using a polymerization initiator comprising the compound represented by Formula 1.

The method for preparing a modified conjugated diene-based polymer may comprise polymerizing conjugated diene-based monomers, or an aromatic vinyl-based monomer and a conjugated diene-based monomer in the presence of a hydrocarbon solvent including a polymerization initiator comprising a compound represented by Formula 1 below to prepare an active polymer combined with an alkali metal (S3); and reacting the active polymer prepared in step (S3) with a modifier (S4).

[Formula 1]

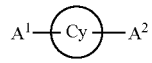

The definition of each substituent in Formula 1 is the same as defined above.

Step (S3) is preparing an active polymer combined with an alkali metal and may be conducted by polymerizing conjugated diene-based monomers, or a conjugated diene-based monomer and an aromatic vinyl-based monomer in the presence of the compound of Formula 1 in a hydrocarbon solvent. The active polymer may represent a polymer in which a polymer anion and an organic metal cation are bonded.

The aromatic vinyl-based monomer may be comprised in an amount of 0.0001 to 50 wt % based on 100 wt % of the total amount of the conjugated diene-based monomer and the aromatic vinyl-based monomer.

The hydrocarbon solvent is not specifically limited, and may be, for example, at least one selected from the group consisting of n-pentane, n-hexane, n-heptane, isooctane, cyclohexane, toluene, benzene and xylene.

The polymerization initiator comprising the compound represented by Formula 1 may be used in an amount of 0.01 mmol to 10 mmol based on total 100 g of the monomers. Particularly, the polymerization initiator may be used in an amount of 0.05 mmol to 5 mmol, more particularly, 0.1 mmol to 2 mmol, further more particularly, 0.1 mmol to 1 mmol based on total 100 g of the monomers.

The polymerization in step (S3) may be conducted after further adding a polar additive, and the polar additive may be added in an amount of 0.001 g to 50 g, particularly, 0.001 g to 10 g, more particularly, 0.005 g to 0.1 g based on total 100 g of the monomers.

In addition, the polar additive may be added in an amount of 0.001 g to 10 g, particularly, 0.005 g to 1 g, more particularly, 0.005 g to 0.1 g based on total 1 mmol of the organic metal compound.

The polar additive may be salts, ethers, amines or a mixture thereof, and particularly, may be at least one selected from the group consisting of tetrahydrofuran, ditetrahydrofurylpropane, diethyl ether, cyclo amalether, dipropyl ether, ethylene dimethyl ether, ethylene dimethyl ether, diethylene glycol, dimethyl ether, tert-butoxy ethoxy ethane bis(3-dimethylaminoethyl)ether, (dimethylaminoethyl) ethyl ether, trimethylamine, triethylamine, tripropylamine, and tetramethylethylenediamine. More particularly, ditetrahydropropylpropane, triethylamine or tetramethylethylenediamine may be used.

In the preparation method according to an embodiment of the present invention, by using the polar additive during the copolymerization of the conjugated diene-based monomers, or the conjugated diene-based monomer and the aromatic vinyl-based monomer, the reaction rate difference may be compensated, thereby inducing the easy formation of a random copolymer.

The polymerization in step (S3) may be anionic polymerization, particularly, living anionic polymerization by which an active part is obtained by the growth reaction of anions.

In addition, the polymerization may be a polymerization with heating, an isothermal polymerization, a polymerization at a fixed temperature (adiabatic polymerization).

Here, the polymerization at a fixed temperature means a polymerization method comprising polymerizing using self-generated heat of reaction without optionally supplying heat after injecting an alkali metal compound. The polymerization with heating means a polymerization method in which the temperature is elevated by optionally supplying heat after injecting the alkali metal compound, and the isothermal polymerization means a polymerization method by which the temperature of a polymer is kept constant by optionally supplying heat or taking heat after injecting the alkali metal compound.

The polymerization may be conducted in a temperature range of −20° C. to 200° C., particularly, 0° C. to 150° C., more particularly, 10° C. to 120° C.

Step (S4) is a step of reacting the active polymer with a modifier to prepare a modified conjugated diene-based polymer.

A modifier having high anion reactivity and thus, may easily act with the active part of a polymer to easily perform modification, may be preferably used as the modifier.

The modifier according to an embodiment of the present invention may comprise a compound represented by Formula 6 below.

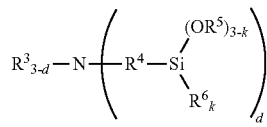

[Formula 6]

In Formula 6, $R^3$ may be an alkyl group or an alkylsilyl group having from 1 to 20 carbon atoms, $R^4$ may be an alkylene group having from 1 to 20 carbon atoms, $R^5$ and $R^6$ may be each independently an alkyl group having from 1 to 20 carbon atoms, k may be 0, 1 or 2, and d may be 1, 2 or 3.

In particular embodiments, the compound represented by Formula 6 may be any one selected from the group consisting of the compounds represented by Formulae 6-1 and 6-2 below.

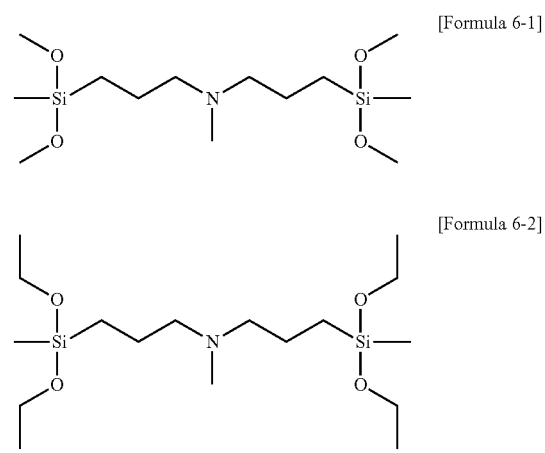

[Formula 6-1]

[Formula 6-2]

In this case, the modified conjugated diene-based polymer comprises a functional group derived from a polymerization initiator at one terminal, and additionally a functional group derived from a modifier comprising the compound represented by Formula 6 at the other terminal, and interaction with an inorganic filler is excellent. In addition, linearity between modified conjugated diene-based polymers which are coupled by the modifier is high, and thus effects of excellent abrasion resistance may be attained.

In another embodiment, the modifier according to an embodiment of the present invention may comprise a compound represented by Formula 7 below.

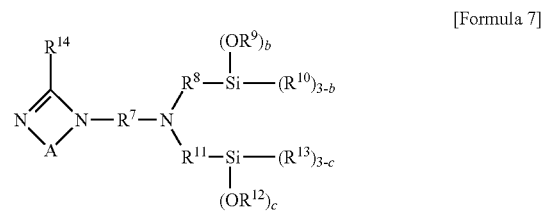

[Formula 7]

In Formula 7, $R^7$, $R^8$ and $R^{11}$ may be each independently an alkylene group having from 1 to 10 carbon atoms, $R^9$, $R^{10}$, $R^{12}$ and $R^{13}$ may be each independently an alkyl group having from 1 to 10 carbon atoms, $R^{14}$ may be hydrogen or an alkyl group having from 1 to 10 carbon atoms, b and c may be each independently 0, 1, 2 or 3, where b+c1, and A may be

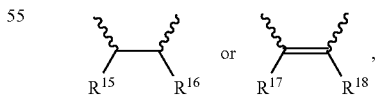

where $R^{15}$, $R^{16}$, $R^{17}$ and $R^{18}$ may be each independently hydrogen, or an alkyl group having from 1 to 10 carbon atoms.

In particular embodiments, the compound represented by Formula 7 may be any one selected from the group consisting of the compounds represented by Formulae 7-1 and 7-2 below.

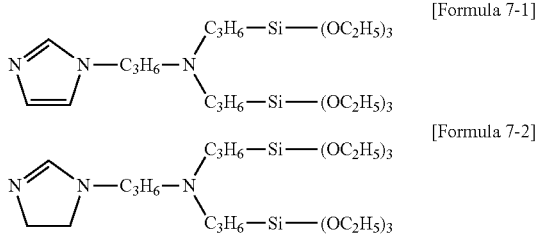

[Formula 7-1]

[Formula 7-2]

In this case, the modified conjugated diene-based polymer comprises a functional group derived from a polymerization initiator at one terminal, and additionally a functional group derived from a modifier comprising the compound represented by Formula 7 at the other terminal, and interaction with an inorganic filler is excellent and effects of excellent tensile properties and viscoelasticity properties may be attained.

In another embodiment, the modifier according to an embodiment of the present invention may comprise a compound represented by Formula 8 below.

[Formula 8]

In Formula 8, $R^{19}$ and $R^{20}$ may be each independently an alkyl group having from 1 to 20 carbon atoms, $R^{21}$ may be one kind of a functional group selected from the group consisting of Formulae 9 to 12 below, e may be 1 or 2, and f may be an integer selected from 0 to 2, where e and f may not be 2 at the same time.

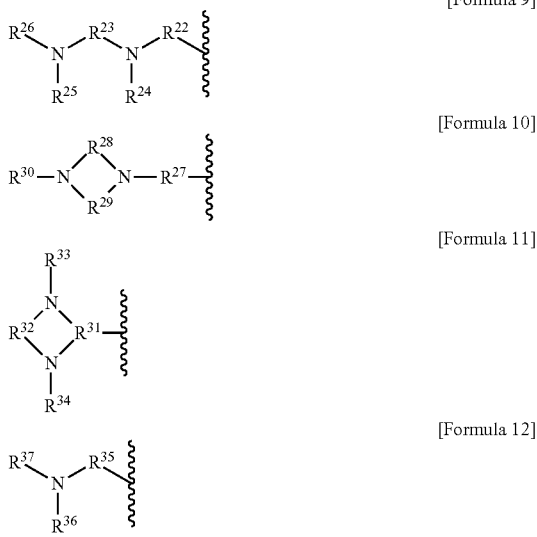

[Formula 9]

[Formula 10]

[Formula 11]

[Formula 12]

In Formulae 9 to 12, $R^{22}$, $R^{23}$, $R^{27}$, $R^{28}$, $R^{29}$, $R^{32}$ and $R^{35}$ may be each independently a linear or branched alkylene group having from 1 to 20 carbon atoms, $R^{24}$, $R^{25}$, $R^{26}$, $R^{30}$, $R^{33}$, $R^{34}$, $R^{36}$ and $R^{37}$ may be each independently an alkyl group or an alkylsilyl group having from 1 to 20 carbon atoms and $R^{31}$ may be a trivalent hydrocarbon group having from 1 to 20 carbon atoms.

In particular embodiments, the compound represented by Formula 8 may be any one selected from the group consisting of Formulae 13 to 17 below.

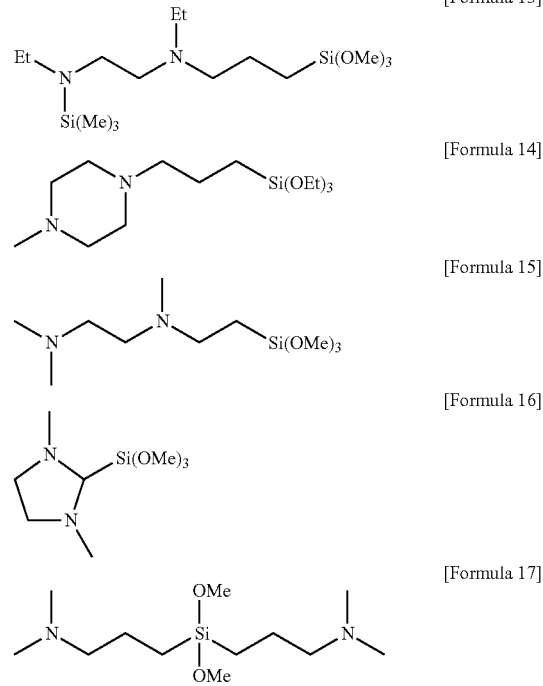

[Formula 13]

[Formula 14]

[Formula 15]

[Formula 16]

[Formula 17]

In Formulae 13 to 17, Me is a methyl group and Et is an ethyl group.

In this case, the modified conjugated diene-based polymer comprises a functional group derived from a polymerization initiator at one terminal, and additionally a functional group derived from a modifier comprising the compound represented by Formula 8 at the other terminal, and interaction with an inorganic filler is excellent and effects of improving tensile properties and viscoelasticity properties may be attained.

The modifier according to an embodiment of the present invention may be one kind or a mixture of at least two kinds, and may be used in the reaction.

The modifier comprising at least one selected from the group consisting of the compounds represented by Formulae 6 to 8 may be used in an amount of 0.1 mol to 10 mol based on 1 mol of a polymerization initiator comprising the compound represented by Formula 1. Particularly, the modifier may be used in an amount of 0.3 mol to 2 mol based on 1 mol of the polymerization initiator. If the modifier is used in an amount in the ratio range, modification reaction of optimum performance may be conducted, and a conjugated diene-based polymer with a high modification ratio may be obtained.

The reaction in step (S4) is a modification reaction for introducing a functional group to a polymer, and may be conducted at 0° C. to 90° C. for 1 minute to 5 hours.

In addition, the preparation method of the modified conjugated diene-based polymer according to an embodiment of the present invention may be conducted by a batch process or a continuous polymerization method comprising at least one reactor.

The preparation method according to an embodiment of the present invention may further comprise at least one step of recovering and drying of solvents and unreacted monomers after step (S4) if needed.

In addition, the modifier may have solubility of 10 g or more with respect to 100 g of a nonpolar solvent, for example, hexane at 25° C. under 1 atm. Here, the solubility of the modifier means the degree of clear dissolution without turbidity when observed with a naked eye. With such a high solubility, an excellent modification ratio with respect to a polymer may be shown.

Meanwhile, the polymerization initiator and the modifier according to the present invention comprises an optimized functional group which may maximize the affinity with an inorganic filler and a solvent, and may be used as the polymerization initiator and the modifier of a conjugated diene-based polymer, thereby serving the conjugated diene-based polymer with the effects of excellent viscoelasticity, tensile properties, wet traction and processability.

Thus, the present invention provides a modified conjugated diene-based polymer comprising a functional group derived from a polymerization initiator represented by Formula 1 at one terminal.

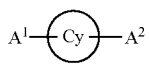
[Formula 1]

The definition of each substituent in Formula 1 is the same as defined above.

In a particular embodiment, the modified conjugated diene-based polymer may comprise a conjugated diene-based polymer chain (P) comprising a functional group derived from a polymerization initiator represented by Formula 1 at one terminal, and may be represented by a compound type represented by Formula 18 below.

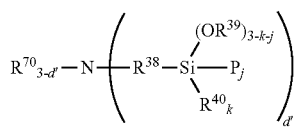
[Formula 18]

In Formula 18, $R^{70}$ may be an alkyl group or an alkylsilyl group having from 1 to 20 carbon atoms, $R^{38}$ may be an alkylene group having from 1 to 20 carbon atoms, $R^{39}$ and $R^{40}$ may be each independently an alkyl group having from 1 to 20 carbon atoms, k may be 0, 1 or 2, k+j may be 1, 2 or 3, and d' may be 1, 2 or 3.

In another embodiment, the modified conjugated diene-based polymer may comprise a conjugated diene-based polymer chain (P) comprising a functional group derived from a polymerization initiator represented by Formula 1 at one terminal, and may be represented by a compound type represented by Formula 19 below.

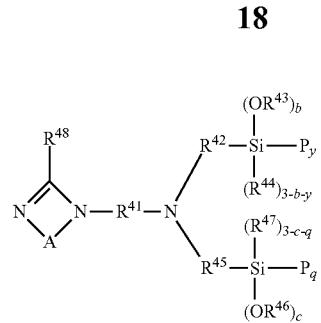
[Formula 19]

In Formula 19, $R^{41}$, $R^{42}$ and $R^{45}$ may be each independently an alkylene group having from 1 to 10 carbon atoms, $R^{43}$, $R^{44}$, $R^{46}$ and $R^{47}$ may be each independently an alkyl group having from 1 to 10 carbon atoms, $R^{48}$ may be hydrogen or an alkyl group having from 1 to 10 carbon atoms, b and c may be each independently 0, 1 or 2, y and q may be each independently 1, 2 or 3, b+y and c+q may be each independently 1, 2 or 3, and A may be

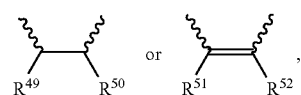

where $R^{49}$, $R^{50}$, $R^{51}$ and $R^{52}$ may be each independently hydrogen or an alkyl group having from 1 to 10 carbon atoms.

In more particular embodiments, the compound represented by Formula 19 may be any one selected from the group consisting of Formula 19-1 and Formula 19-2 below.

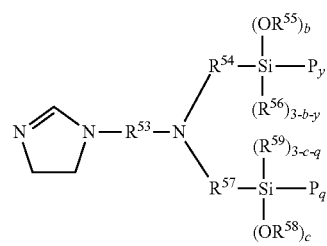
[Formula 19-1]

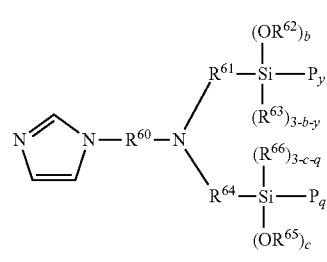
[Formula 19-2]

In Formula 19-1 and Formula 19-2, $R^{55}$, $R^{56}$, $R^{58}$, $R^{59}$, $R^{62}$, $R^{63}$, $R^{65}$ and $R^{66}$ may be each independently an alkyl group having from 1 to 10 carbon atoms, $R^{53}$, $R^{54}$, $R^{57}$, $R^{60}$, $R^{61}$ and $R^{64}$ may be each independently an alkylene group having from 1 to 10 carbon atoms, b and c may be each independently 0, 1 or 2, y and q may be each independently 1, 2 or 3, and b+y and c+q may be each independently 1, 2 or 3.

In another embodiment, the modified conjugated diene-based polymer may comprise a conjugated diene-based polymer chain (P) comprising a functional group derived from a polymerization initiator represented by Formula 1 at one terminal, and may be represented by a compound type represented by Formula 20 below.

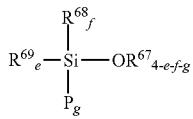
[Formula 20]

In Formula 20, $R^{67}$ and $R^{68}$ may be each independently an alkyl group having from 1 to 20 carbon atoms, $R^{69}$ may be one kind of a functional group selected from the group consisting of Formulae 9 to 12 below, e may be 1 or 2, f may be 0 or 1, and g may be an integer selected from 1 to 3.

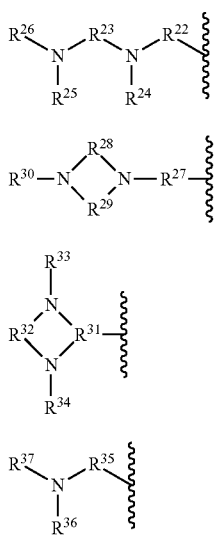

[Formula 9]

[Formula 10]

[Formula 11]

[Formula 12]

In Formulae 9 to 12, $R^{22}$, $R^{23}$, $R^{27}$, $R^{28}$, $R^{29}$, $R^{32}$ and $R^{35}$ may be each independently a linear or branched alkylene group having from 1 to 20 carbon atoms, $R^{24}$, $R^{25}$, $R^{26}$, $R^{30}$, $R^{33}$, $R^{34}$, $R^{36}$ and $R^{37}$ may be each independently an alkyl group or an alkylsilyl group having from 1 to 20 carbon atoms, and $R^{31}$ may be a trivalent hydrocarbon group having from 1 to 20 carbon atoms.

In more particular embodiments, the compound represented by Formula 20 may be any one selected from the group consisting of the compounds represented by Formulae 21 to 25 below.

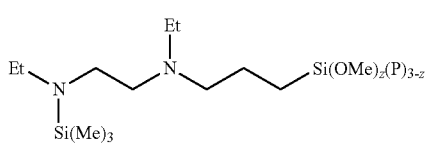
[Formula 21]

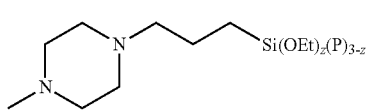
[Formula 22]

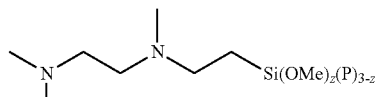
[Formula 23]

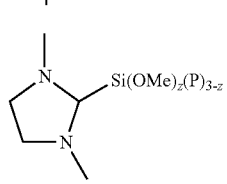
[Formula 24]

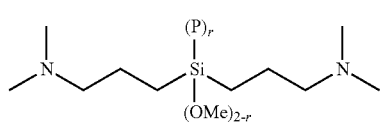
[Formula 25]

In Formulae 21 to 25, Me is a methyl group, Et is an ethyl group, z may be 0, 1 or 2, and r may be 1 or 2.

The conjugated diene-based polymer chain may be derived from a homopolymer of conjugated diene-based monomers or a copolymer of a conjugated diene-based monomer and an aromatic vinyl-based monomer. Accordingly, the conjugated diene-based polymer according to an embodiment of the present invention may comprise a derived unit from a conjugated diene-based monomer and a derived unit from an aromatic vinyl-based monomer.

In the present invention, the terms "derived unit" may denote a component or a structure come from a certain material, or may denote the material itself.

Meanwhile, the modified conjugated diene-based polymer may be a homopolymer or a copolymer. If the modified conjugated diene-based polymer is the homopolymer, the modified conjugated diene-based polymer may be a modified conjugated diene polymer, and if the modified conjugated diene-based polymer is the copolymer, the modified conjugated diene-based polymer may comprise a derived unit from a conjugated diene-based monomer and a derived unit from an aromatic vinyl-based monomer. In addition, if the modified conjugated diene-based polymer is the copolymer, the copolymer may be a random copolymer.

In the present invention, the terms "random copolymer" may denote a copolymer in which the constituent units thereof are arranged in disorder.

The conjugated diene-based monomer may be, for example, at least one selected from the group consisting of 1,3-butadiene, 2,3-dimethyl-1,3-butadiene, piperylene, 3-butyl-1,3-octadiene, isoprene, and 2-phenyl-1,3-butadiene, without specific limitation.

If the modified conjugated diene-based polymer is the copolymer, the derived unit from the conjugated diene-based monomer may be comprised in an amount of 50 wt % or more, particularly, 60 wt % to 90 wt %, more particularly, 60 wt % to 85 wt %.

The aromatic vinyl-based monomer may be, for example, at least one selected from the group consisting of styrene, α-methyl styrene, 3-methyl styrene, 4-methyl styrene, 4-propylstyrene, 1-vinylnaphthalene, 4-cyclohexylstyrene, 4-(p-methylphenyl)styrene and 1-vinyl-5-hexylnaphthalene, without specific limitation.

In the case where the modified conjugated diene-based polymer is the copolymer, the derived unit from the aromatic vinyl-based monomer may be comprised in an amount of 50 wt % or less, particularly, 0.0001 wt % to 50 wt %, more particularly, 15 wt % to 40 wt %.

In addition, the modified conjugated diene-based polymer may have a number average molecular weight of 10,000 g/mol to 10,000,000 g/mol, particularly, 100,000 g/mol to 2,000,000 g/mol, more particularly, 120,000 g/mol to 1,500,000 g/mol.

The modified conjugated diene-based polymer may have molecular weight distribution (Mw/Mn) of 1.0 to 8.0, particularly, 1.0 to 4.0, more particularly, 1.0 to 3.5. If the modified conjugated diene-based polymer has the above-mentioned molecular weight distribution, a rubber composition comprising the same may have improved processability, and as a result, the mechanical properties, the low fuel consumption ratio and the abrasion resistance of a produced molded article may be improved.

In addition, the modified conjugated diene-based polymer may have a vinyl content of 5 wt % or more, particularly, 10 wt % or more, more particularly, 14 wt % to 70 wt %. If the vinyl content of the modified conjugated diene-based polymer is in the range, a glass transition temperature may be controlled in an appropriate range. Accordingly, when applied to tires, physical properties required for tires such as running resistance and braking force may be satisfied, and fuel consumption reducing effects may be attained.

Here, the vinyl content represents the amount of not 1,4-added but 1,2-added conjugated diene-based monomer based on 100 wt % of a conjugated diene-based polymer composed of a vinyl group-comprising monomer and an aromatic vinyl-based monomer.

In addition, in view of the viscoelasticity of the modified conjugated diene-based polymer when taking measurements after mixing silica via DMA with 10 Hz, a Tan δ value at 0° C. (Tan δ at 0° C.) is from 0.4 to 1, or from 0.5 to 1, and in this range, effects of markedly improving surface resistance or wet resistance may be attained when compared to the conventional invention.

In addition, a Tan δ value at 60° C. (Tan δ at 60° C.) may be from 0.3 to 0.2, or from 0.15 to 0.1, and in this range, effects of markedly improving running resistance, wet traction or rolling resistance (RR) may be attained when compared to the conventional invention.

In addition, the modified conjugated diene-based polymer may comprise from 0.00001 wt % to 0.001 wt % of a silyl group based on the total mol number of the polymer.

In addition, the present invention provides a rubber composition comprising the modified conjugated diene-based polymer.

The rubber composition according to an embodiment of the present invention may comprise the modified conjugated diene-based polymer in an amount of 10 wt % or more, particularly, 10 wt % to 100 wt %, more particularly, 20 wt % to 90 wt %. If the amount of the modified conjugated diene-based polymer is less than 10 wt %, the improving effects of abrasion resistance and crack resistance of a molded article manufactured by using the rubber composition, for example, a tire may be insignificant.

In addition, the rubber composition may further comprise other rubber component, if needed, in addition to the modified conjugated diene-based polymer, and, in this case, the rubber component may be comprised in an amount of wt % or less based on the total amount of the rubber composition. Particularly, the rubber composition may comprise the rubber component in an amount of 1 part by weight to 900 parts by weight based on 100 parts by weight of the modified conjugated diene-based polymer.

The rubber component may be a natural rubber or a synthetic rubber, and the rubber component may be, for example, a natural rubber (NR) comprising cis-1,4-polyisoprene; a modified natural rubber which is obtained by modifying or purifying a common natural rubber, such as an epoxidized natural rubber (ENR), a deproteinized natural rubber (DPNR), and a hydrogenated natural rubber; and a synthetic rubber such as a styrene-butadiene copolymer (SBR), polybutadiene (BR), polyisoprene (IR), a butyl rubber (IIR), an ethylene-propylene copolymer, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), a polysulfide rubber, an acryl rubber, a urethane rubber, a silicone rubber, an epichlorohydrin rubber, a butyl rubber, a halogenated butyl rubber, and any one or a mixture of at least two thereof may be used.

In addition, the rubber composition may comprise 0.1 parts by weight to 200 parts by weight of a filler, particularly, 10 parts by weight to 120 parts by weight of a filler based on 100 parts by weight of a modified conjugated diene-based polymer.

The filler may be a silica-based filler, and the silica-based filler may be, for example, wet silica (hydrated silicate), dry silica (anhydrous silicate), calcium silicate, aluminum silicate, or colloid silica, without specific limitation. More particularly, the filler may be wet silica which has the most significant compatible effects of improving effects of destruction characteristics and wet grip characteristics.

In addition, the rubber composition according to an embodiment of the present invention may further comprise a carbon black-based filler if needed.

Meanwhile, if the silica is used as the filler, a silane coupling agent may be used together for the improvement of reinforcing and low exothermic properties.

The silane coupling agent may particularly comprise bis(3-triethoxysilylpropyl)tetrasulfide, bis(3-triethoxysilylpropyl)trisulfide, bis(3-triethoxysilylpropyl)disulfide, bis(2-triethoxysilylethyl)tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl)tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and any one or a mixture of at least two thereof may be used. More particularly, the silane coupling agent may be bis(3-triethoxysilylpropyl)polysulfide or 3-trimethoxysilylpropylbenzothiazyltetrasulfide in consideration of the improving effects of reinforcing properties.

In addition, in the rubber composition according to an embodiment of the present invention, a modified conjugated diene-based polymer in which a functional group having high affinity with silica is introduced at an active part as a rubber component is used, and the compounding amount of a silane coupling agent may be smaller than a common case. Particularly, the silane coupling agent may be used in an amount of 1 part by weight to 20 parts by weight based on 100 parts by weight of silica. If used in the above range, effects as a coupling agent may be sufficiently exhibited, and the gelation of a rubber component may be prevented. More particularly, the silane coupling agent may be used in an amount of 5 parts by weight to 15 parts by weight based on 100 parts by weight of silica.

In addition, the rubber composition according to an embodiment of the present invention may be sulfur cross-linkable, and so, may further comprise a vulcanizing agent. The vulcanizing agent may be particularly a sulfur powder and may be comprised in an amount of 0.1 parts by weight to 10 parts by weight based on 100 parts by weight of a rubber component. With the amount in the above range, elasticity and strength required for a vulcanized rubber composition may be secured, and at the same time, a low fuel consumption ratio may be attained.

In addition, the rubber composition according to an embodiment of the present invention may further comprise various additives used in a common rubber industry in addition to the above components, particularly, a vulcanization accelerator, a process oil, a plasticizer, an antiaging agent, a scorch preventing agent, a zinc white, stearic acid, a thermosetting resin, a thermoplastic resin, or the like.

The vulcanization accelerator is not specifically limited and may particularly comprise thiazole-based compounds such as 2-mercaptobenzothiazole (M), dibenzothiazyldisulfide (DM), and N-cyclohexyl-2-benzothiazylsulfenamide (CZ), or guanidine-based compounds such as diphenylguanidine (DPG). The vulcanization accelerator may be comprised in an amount of 0.1 parts by weight to 5 parts by weight based on 100 parts by weight of the rubber component.

In addition, the process oil acts as a softener in a rubber composition and may particularly comprise a paraffin-based, naphthene-based, or aromatic compound. More particularly, an aromatic process oil may be used in consideration of tensile strength and abrasion resistance, and a naphthene-based or paraffin-based process oil may be used in consideration of hysteresis loss and low temperature properties. The process oil may be comprised in an amount of 100 parts by weight or less based on 100 parts by weight of the rubber component. With the above-described amount, the deterioration of tensile strength and low exothermic properties (low fuel consumption ratio) of the vulcanized rubber may be prevented.

In addition, the antiaging agent may particularly comprise N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a condensate of diphenylamine and acetone at a high temperature. The antiaging agent may be used in an amount of 0.1 parts by weight to 6 parts by weight based on 100 parts by weight of the rubber component.

The rubber composition according to an embodiment of the present invention may be obtained by mulling using a mulling apparatus such as a banbury mixer, a roll, and an internal mixer according to a mixing prescription. In addition, a rubber composition having low exothermic properties and good abrasion resistance may be obtained due to a vulcanization process after a molding process. Therefore, the rubber composition may be useful to the manufacture of each member of a tire such as a tire tread, an under tread, a side wall, a carcass coating rubber, a belt coating rubber, a bead filler, a chafer, and a bead coating rubber, or to the manufacture of rubber products in various industries such as a dustproof rubber, a belt conveyor, and a hose.

Also, there is provided in the present invention a tire manufactured using the rubber composition. The tire may comprise a tire or a tire tread.

The invention claimed is:

1. A polymerization initiator comprising a compound represented by the following Formula 1:

[Formula 1]

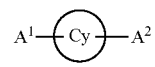

in Formula 1,
Cy is a cyclic saturated hydrocarbon group having from 5 to 8 carbon atoms, which is unsubstituted or substituted with an alkyl group having from 1 to 4 carbon atoms, and A1 and A2 are each independently a functional group represented by the following Formula 2:

[Formula 2]

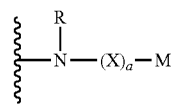

in Formula 2,
R is a linear hydrocarbon group having from 1 to 20 carbon atoms, or a monocyclic or multicyclic saturated hydrocarbon group having from 3 to 20 carbon atoms, X is a divalent hydrocarbon group having from 1 to 5 carbon atoms, M is an alkali metal, and a is 0 or 1.

2. The polymerization initiator of claim 1, wherein the compound represented by Formula 1 is a compound represented by the following Formula 3:

[Formula 3]

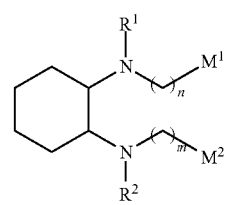

in formula 3,
R1 and R2 are each independently a linear hydrocarbon group having from 1 to 20 carbon atoms, or a monocyclic or multicyclic saturated hydrocarbon group having from 4 to 20 carbon atoms, M1 and M2 are each independently an alkali metal, and m and n are each independently an integer selected from 0 to 5.

3. The polymerization initiator of claim 2, wherein in Formula 3,
R1 and R2 are each independently an alkyl group having from 1 to 6 carbon atoms, and M1 and M2 are each independently any one selected from the group consisting of Li, Na and K.

4. The polymerization initiator of claim 2, wherein the compound represented by Formula 3 is any one selected from the group consisting of compounds represented by the following Formulae 3-1 to 3-4:

[Formula 3-1]

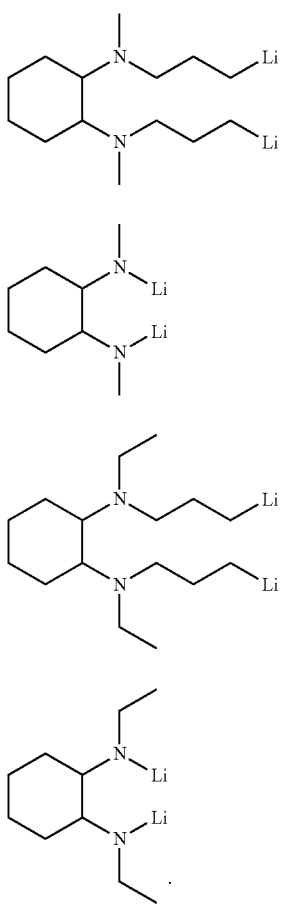

[Formula 3-2]

[Formula 3-3]

[Formula 3-4]

5. A method for preparing a polymerization initiator, the method comprising:

reacting a compound represented by the following Formula 1a and a compound represented by Formula 4 in a solvent to prepare a compound represented by Formula 1b (S1); and reacting the compound represented by Formula 1b and an alkali metal or a compound represented by the following Formula 5 (S2):

[Formula 1a]

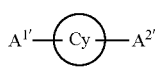

[Formula 1b]

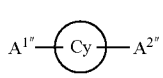

in Formulae 1a and 1b,

Cy is a cyclic saturated hydrocarbon group having from 5 to 8 carbon atoms, which is unsubstituted or substituted with an alkyl group having from 1 to 4 carbon atoms, $A^{1'}$ and $A^{2'}$ are each independently a functional group represented by the following Formula 2a, and $A^{1''}$ and $A^{2''}$ are each independently a functional group represented by the following Formula 2b:

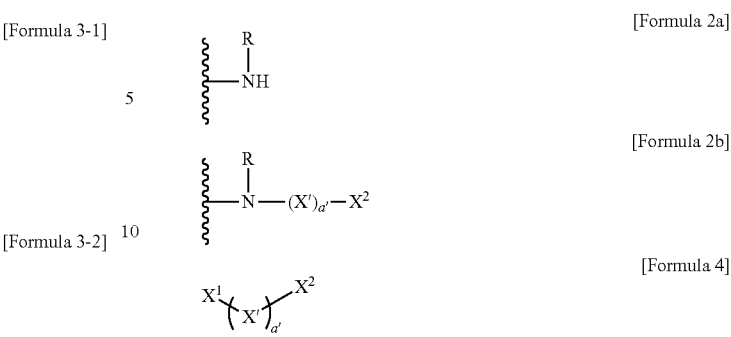

in Formulae 2a, 2b and 4,

R is a linear hydrocarbon group having from 1 to 20 carbon atoms, or a monocyclic or multicyclic saturated hydrocarbon group having from 3 to 20 carbon atoms, X' is a divalent hydrocarbon group having from 1 to 5 carbon atoms, a' is 0 or 1, and $X^1$ and $X^2$ are each independently a halogen compound, $R'(M)_x$  [Formula 5]

in Formula 5,

R' is a hydrocarbyl group having from 1 to 20 carbon atoms, M is an alkali metal, and x is an integer selected from 1 to 4.

6. The method for preparing the polymerization initiator of claim 5, wherein a molar ratio of the compound represented by Formula 1a and the compound represented by Formula 4 in step (S1) is from 1:1 to 1:4.

7. The method for preparing the polymerization initiator of claim 5, wherein a molar ratio of the compound represented by Formula 1b and the alkali metal in step (S2) is 1:10 to 1:40.

8. The method for preparing the polymerization initiator of claim 5, wherein a molar ratio of the compound represented by Formula 1b and the compound represented by Formula 5 in step (S2) is from 1:1.9 to 1:2.2.

9. A method for preparing a modified conjugated diene-based polymer, the method comprising:

polymerizing conjugated diene-based monomers, or an aromatic vinyl-based monomer and a conjugated diene-based monomer in a hydrocarbon solvent including a polymerization initiator comprising a compound represented by the following Formula 1 to prepare an active polymer which is combined with an alkali metal (S3); and reacting the active polymer prepared in step (S3) with a modifier (S4):

[Formula 1]

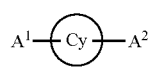

in Formula 1,

Cy is a cyclic saturated hydrocarbon group having from 5 to 8 carbon atoms, which is unsubstituted or substituted with an alkyl group having from 1 to 4 carbon atoms, and $A^1$ and $A^2$ are each independently a functional group represented by the following Formula 2:

[Formula 2]

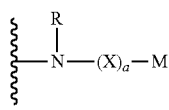

in Formula 2,

R is a linear hydrocarbon group having from 1 to 20 carbon atoms, or a cyclic saturated hydrocarbon group having from 3 to 20 carbon atoms, X is a divalent hydrocarbon group having from 1 to 5 carbon atoms, M is an alkali metal, and a is 0 or 1.

10. The method for preparing the modified conjugated diene-based polymer of claim 9, wherein the modifier is any one selected from the group consisting of compounds represented by the following Formula 6 to 87:

[Formula 6]

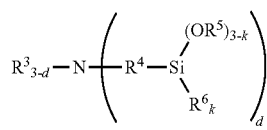

in Formula 6,

R3 is an alkyl group or an alkylsilyl group having from 1 to 20 carbon atoms,

R4 is an alkylene group having from 1 to 20 carbon atoms,

R5 and R6 are each independently an alkyl group having from 1 to 20 carbon atoms, k is 0, 1 or 2, and d is 1, 2 or 3,

[Formula 7]

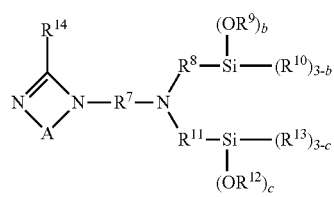

in Formula 7, $R^7$, $R^8$ and $R^{11}$ are each independently an alkylene group having 1 to 10 carbon atoms, $R^9$, $R^{10}$, $R^{12}$ and $R^{13}$ are each independently an alkyl group having 1 to 10 carbon atoms, $R^{14}$ is hydrogen or an alkyl group having from 1 to 10 carbon atoms, and b and c are each independently 0, 1, 2 or 3, where b+c≥1, A is

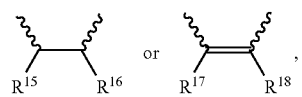

where $R^{15}$, $R^{16}$, $R^{17}$ and $R^{18}$ are each independently hydrogen, or an alkyl group having from 1 to 10 carbon atoms,

[Formula 8]

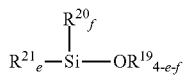

in Formula 8, $R^{19}$ and $R^{20}$ are each independently an alkyl group having from 1 to 20 carbon atoms, $R^{21}$ is a functional group selected from the group consisting of the following Formulae 9 to 12, e is 1 or 2, and f is an integer selected from 0 to 2, where e and f are not 2 at the same time:

[Formula 9]

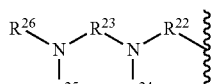

[Formula 10]

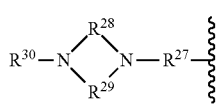

[Formula 11]

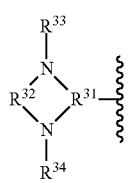

[Formula 12]

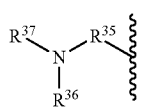

in Formulae 9 to 12, $R^{22}$, $R^{23}$, $R^{27}$, $R^{28}$, $R^{29}$, $R^{32}$ and $R^{35}$ are each independently a linear or branched alkylene group having from 1 to 20 carbon atoms, $R^{24}$, $R^{25}$, $R^{26}$, $R^{30}$, $R^{33}$, $R^{34}$, $R^{36}$, and $R^{37}$ are each independently an alkyl group or an alkylsilyl group having from 1 to 20 carbon atoms, and R31 is a trivalent hydrocarbon group having from 1 to 20 carbon atoms.

11. The method for preparing the modified conjugated diene-based polymer of claim 10, wherein the compound represented by Formula 6 is any one selected from the group consisting of compounds represented by the following Formulae 6-1 and 6-2:

[Formula 6-1]

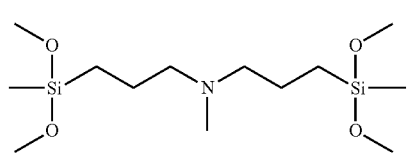

[Formula 6-2]

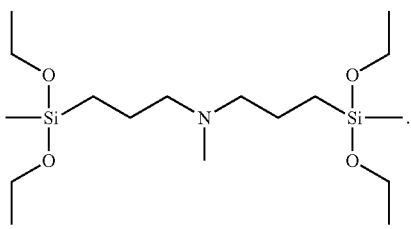

12. The method for preparing the modified conjugated diene-based polymer of claim 10, wherein the compound represented by Formula 7 is any one selected from the group consisting of the following Formulae 7-1 and 7-2:

[Formula 7-1]
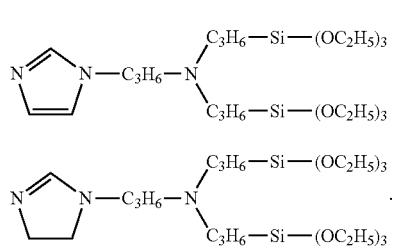

[Formula 7-2]
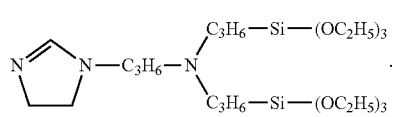

13. The method for preparing the modified conjugated diene-based polymer of claim 10, wherein the compound represented by Formula 8 is any one selected from the group consisting of the following Formulae 13 to 17:

[Formula 13]
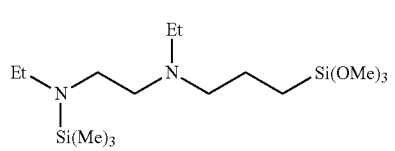

[Formula 14]
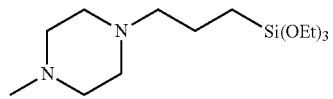

[Formula 15]
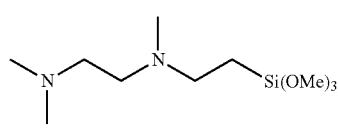

[Formula 16]
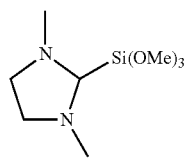

[Formula 17]
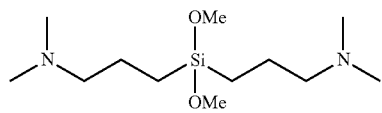

in Formulae 13 to 17, Me is a methyl group, and Et is an ethyl group.

14. The method for preparing the modified conjugated diene-based polymer of claim 9, wherein a molar ratio of the compound represented by Formula 1 and the modifier is from 1:0.1 to 1:10.

15. A modified conjugated diene-based polymer comprising a functional group derived from a polymerization initiator represented by the following Formula 1 at one terminal:

[Formula 1]
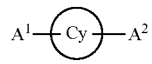

in Formula 1,

Cy is a cyclic saturated hydrocarbon group having from 5 to 8 carbon atoms, which is unsubstituted or substituted with an alkyl group having from 1 to 4 carbon atoms, and $A^1$ and $A^2$ are each independently a functional group represented by the following Formula 2:

[Formula 2]
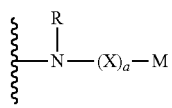

in Formula 2,

R is a linear hydrocarbon group having from 1 to 20 carbon atoms, or a cyclic saturated hydrocarbon group having from 3 to 20 carbon atoms, X is a divalent hydrocarbon group having from 1 to 5 carbon atoms, M is an alkali metal, and a is 0 or 1.

16. The modified conjugated diene-based polymer of claim 15, wherein the modified conjugated diene-based polymer comprises a conjugated diene-based polymer chain (P) comprising a functional group derived from a polymerization initiator represented by Formula 1 at one terminal, the modified conjugated diene-based polymer being any one selected from the group consisting of compounds represented by the following Formula 18 to 20:

[Formula 18]
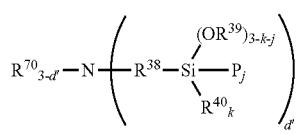

in Formula 18, $R^{70}$ is an alkyl group or an alkylsilyl group having from 1 to 20 carbon atoms, $R^{38}$ is an alkylene group having from 1 to 20 carbon atoms, $R^{39}$ and $R^{40}$ are each independently an alkyl group having from 1 to 20 carbon atoms, k is 0, 1 or 2, k+j is 1, 2 or 3, and d' is 1, 2 or 3,

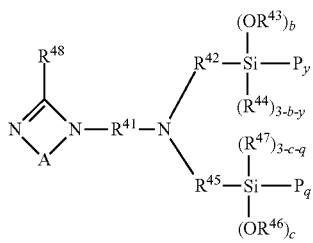

[Formula 19]

in Formula 19, $R^{41}$, $R^{42}$ and $R^{45}$ are each independently an alkylene group having from 1 to 10 carbon atoms, $R^{43}$, $R^{44}$, $R^{46}$ and $R^{47}$ are each independently an alkyl group having from 1 to 10 carbon atoms, R48 is hydrogen or an alkyl group having from 1 to 10 carbon atoms, b and c are each independently 0, 1 or 2, y and q are each independently 1, 2 or 3, and b+y and c+q are each independently 1, 2 or 3, and A is

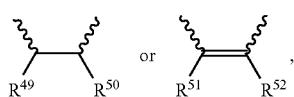

where $R^{49}$, $R^{50}$, $R^{51}$ and $R^{52}$ are each independently hydrogen or an alkyl group having from 1 to 10 carbon atoms

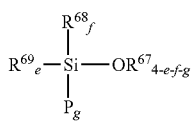

[Formula 20]

in Formula 20, $R^{67}$ and $R^{68}$ are each independently an alkyl group having from 1 to 20 carbon atoms, $R^{69}$ is a functional group selected from the group consisting of the following Formulae 9 to 12, e is 1 or 2, f is 0 or 1, and g is an integer selected from 1 to 3:

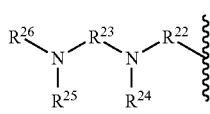

[Formula 9]

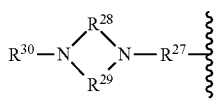

[Formula 10]

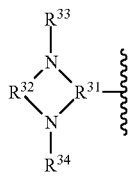

[Formula 11]

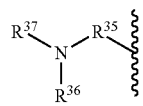

[Formula 12]

in Formulae 9 to 12, $R^{22}$, $R^{23}$, $R^{27}$, $R^{28}$, $R^{29}$, $R^{32}$ and $R^{35}$ are each independently a linear or branched alkylene group having from 1 to 20 carbon atoms, $R^{24}$, $R^{25}$, $R^{26}$, $R^{30}$, $R^{33}$, $R^{34}$, $R^{36}$ and $R^{37}$ are each independently an alkyl group having from 1 to 20 carbon atoms or an alkylsilyl group having from 1 to 20 carbon atoms, and $R^{31}$ is a trivalent hydrocarbon group having from 1 to 20 carbon atoms.

17. The modified conjugated diene-based polymer of claim 16, wherein the compound represented by Formula 19 is any one selected from the group consisting of compounds represented by the following Formulae 19-1 and 19-2:

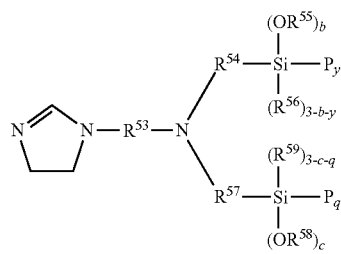

[Formula 19-1]

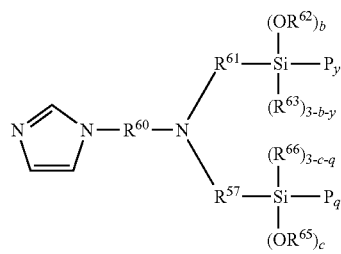

[Formula 19-2]

in Formulae 19-1 and 19-2, $R^{55}$, $R^{56}$, $R^{58}$, $R^{59}$, $R^{62}$, $R^{63}$, $R^{65}$ and $R^{66}$ are each independently an alkyl group having from 1 to 10 carbon atoms, $R^{53}$, $R^{54}$, $R^{57}$, $R^{60}$, $R^{61}$ and $R^{64}$ are each independently an alkylene group having from 1 to 10 carbon atoms, b and c are each independently 0, 1 or 2, y and q are each independently 1, 2 or 3, b+y and c+q are each independently 1, 2 or 3.

18. The modified conjugated diene-based polymer of claim 16, wherein the compound represented by Formula 20 is any one selected from the group consisting of the following Formulae 21 to 25:

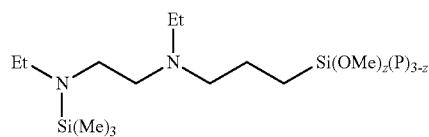

[Formula 21]

[Formula 22]
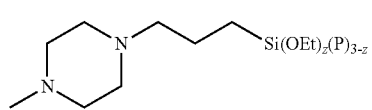
[Formula 23]
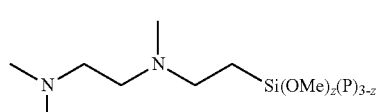
[Formula 24]
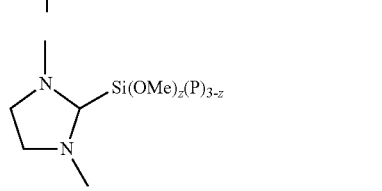
[Formula 25]
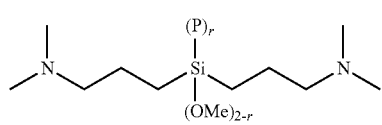
in Formulae 21 to 25,
Me is a methyl group, Et is an ethyl group, z is 0, 1 or 2, and r is 1 or 2.
* * * * *